(12) United States Patent
Brothier et al.

(10) Patent No.: US 7,968,055 B2
(45) Date of Patent: Jun. 28, 2011

(54) DEVICE AND METHOD FOR CONTINUOUS MEASUREMENT OF CONCENTRATIONS OF TARS IN A GAS FLOW

(75) Inventors: Meryl Brothier, Aix En Provence (FR); Pierre Estubier, Manosque (FR); Johann Soyez, Aubagne (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 12/518,316

(22) PCT Filed: Dec. 27, 2007

(86) PCT No.: PCT/EP2007/064562
§ 371 (c)(1), (2), (4) Date: Oct. 28, 2009

(87) PCT Pub. No.: WO2008/080931
PCT Pub. Date: Jul. 10, 2008

(65) Prior Publication Data
US 2010/0043528 A1    Feb. 25, 2010

(30) Foreign Application Priority Data
Dec. 28, 2006  (FR) ...................................... 06 56007

(51) Int. Cl.
*G01N 5/02* (2006.01)
(52) U.S. Cl. ............. 422/83; 422/88; 422/94; 73/23.33; 73/28.01; 73/28.04
(58) Field of Classification Search .................... None
See application file for complete search history.

(56) References Cited

U.S. PATENT DOCUMENTS

| 5,415,025 A | 5/1995 | Bartman et al. |
| 5,703,360 A | 12/1997 | Fischer et al. |
| 2002/0048818 A1 | 4/2002 | Sakairi et al. |

FOREIGN PATENT DOCUMENTS

DE         160 249 A3    5/1983

(Continued)

OTHER PUBLICATIONS

Zhu, Guangzhong et al. "A study of acidity and coke deposits on NiHZSM-5 catalyst in aromatization." React. Kinet. Catal. Lett. (1999) 66 231-236.*

(Continued)

*Primary Examiner* — Yelena G Gakh
*Assistant Examiner* — Christopher A Hixson
(74) *Attorney, Agent, or Firm* — Pearne & Gordon LLP (57) ABSTRACT

The measurement is conducted by means of thermogravimetric scales (10) bearing at one end of the beam (20) a catalyst body (30) for catalysing a coking reaction of the tars present in the gas state. Precautions are taken in order to ensure homogeneity and regularity of the sampled gas flow and to guarantee predominant catalysis on the catalytic body (30), the weight increase of which gives the weight of the deposited coke and indirectly the content of tars present in the gas state in the gas to be measured. A calorimetric device (34) for analyzing gases from the coking of the tars provides a complementary and/or additional measurement. The solid tars are filtered beforehand, but their content may be measured by an auxiliary device.
Possible application to analyzing gases from biomass.

18 Claims, 6 Drawing Sheets

FOREIGN PATENT DOCUMENTS

| | | |
|---|---|---|
| DE | 1602 49 A1 | 5/1983 |
| DE | 198 32 411 A1 | 3/1999 |
| EP | 0 586 012 A2 | 3/1994 |
| EP | 1 102 004 A1 | 5/2001 |
| JP | 2005-274502 A | 10/2005 |
| WO | 03/054246 A1 | 7/2003 |
| WO | 2006/014555 A1 | 2/2006 |

OTHER PUBLICATIONS

Echard, Michael et al. "Sulphidation of an oxidic CoMo/Al2O3 catalyst under practical conditions: different kinds of sulphur species." Catalysis Letters (2001) 72 83-89.*

Broutin et al; "Anticoking Coatings for High Temperature Petrochemical Reactors", Oil & Gas Science and Technology—Rev. IFP, vol. 54 (1999) No. 3, pp. 375-385.

Pindoria et al; "A two-stage fixed-bed reactor for direct hydrotreatment of volatiles from the hydropyrolysis of biomass: effect of catalyst temperature, pressure and catalyst ageing time on product characteristics", Fuel, vol. 77, No. 15, Dec. 1, 1998 pp. 1715-1726.

Xu et al; "Comparison of a Solvent-Free Tar Quantification Method to the International Energy Agency's Tar Managment Protocol", Energy & Fuels 2005, pp. 2509-2513.

Carpenter et al; "Quantitative Measurement of Biomass Gasifier Tars Using a Molecular-Beam Mass Spectrometer: Comparison with Traditional Impinger Sampling", Energy & Fuels 2007, No. 21, pp. 3036-3043.

Bain et al; "Evaluation of Catalyst Deactivation during Catalytic Steam Reforming of Biomass-Derived Syngas", Industrial and Engineering Chemistry Research, vol. 44, No. 21 Oct. 12, 2005 pp. 7945-7956.

French Search Report for FR 709590 dated Apr. 19, 2009.
French Search Report for FR 709589 dated Apr. 19, 2009.
International Search Report for PCT/EP2007/064639.
International Search Report for PCT/EP2007/064562.

* cited by examiner

DEVICE AND METHOD FOR CONTINUOUS MEASUREMENT OF CONCENTRATIONS OF TARS IN A GAS FLOW

TECHNICAL FIELD

The present invention relates to the field of techniques for analyzing and measuring pollutants in a gas flow.

More particularly, it relates to a device and a method for continuously measuring tars of a gas, these tars being able to be traces and at high temperatures (T>800° C.).

STATE OF THE PRIOR ART

One of the major problems encountered in vapo-gasification is to be able to continuously assess the quality of the generated gas in order to make sure that the latter complies with specifications required by its application (generation of electricity, of mechanical energy, of heat, synthesis of fuels or other chemical products or further formation of hydrogen).

Assessing the specifications of synthesis gas requires knowledge of the composition of the gas and therefore i.a. the concentration of the different pollutant species; these are sulfur-, nitrogen-, chlorine-containing compounds, alkaline metals, dusts and tars.

The presence of tars in gases derived from gasification poses many problems in the different targeted applications, such as for example deterioration of the blades of turbines or further the loss of activity of catalysts by inactivation, notably as regards metal and zeolite catalysts. Tars may pose other problems notably in pyrolysis or gasification reactors where under the action of heat, they give rise to a deposit of heavy hydrocarbon compounds, called coke, on the walls of the reactor; this phenomenon bearing the name of coking. As a result of this deposit, transfers of heat to the reactor are thereby reduced. Formation of coke also tends to increase pressure losses in the conduits and in the absence of corrective action ends with blocking the ducts. Coke stems from a complex mechanism which is broken down into parts: a catalytic sequence and a thermal sequence.

There is therefore a real industrial need for having a device and a method for measuring tar traces which is both quantitative, continuous and on-line.

Moreover, tars, as byproducts of the heat degradation of organic material, are good indicators in terms of follow-up of vapo-gasification methods. Thus, the continuous measurement of the concentration of tars or at the very least the tracking of the concentration of tracers, representative molecules of categories of tars, may be a control tool for gasification methods with view to real time optimization of the parameters of the latter.

Now, the measurement of the content of tars, present as traces in the gas flow, is subject to many difficulties.

A first difficulty is related to the meaning of the generic term <<tar>> which differs according to the relevant field of application. Within the scope of atmospheric pollution, of metallurgy, of waste incineration, of cogeneration and production of synthetic fuels, by <<tars>> are generally designated the whole of the organic compounds having a molecular mass above that of benzene—i.e. 78 g/mol—but there is no official definition for this term, and the literature reports about thirty definitions for the word <<tar>>, the meaning of which is still today subject to discussions. As an indication, we may cite a few of these definitions: <<mixture of chemical compounds condensing on metal surfaces at room temperature>> or further <<the whole of the components having a boiling temperature above 150° C.>>.

Tars cover a wide spectrum of species (more than 2,000), the physicochemical characteristics of which (polarity, volatility, molar mass, chemical affinity) vary over a large range of values, which makes it particularly difficult to obtain a measurement reporting the total tar content. Several classifications of these various compounds have been proposed today as for example the classification of Milne & Evans (1998) which lists the different tars in three classes:
 Class 1: primary species,
 Class 2: secondary species,
 Class 3: tertiary species.

The main components are polycyclic aromatic hydrocarbons (PAH), volatile organic compounds (VOC) and phenols.

There exist various techniques for measuring tars but the latter only partly meet the measurement needs.

For this purpose, it is desirable to have a device and a method which simultaneously fulfill the following functions:
 carry out a measurement of tars present as traces (at concentrations of the order of $mg/Nm^3$ or even less) in a gas matrix;
 carry out a quantitative measurement of the whole of the tars, regardless of their physical states. Indeed, in order to estimate the quality of the gas, it is absolutely necessary that the measurement be representative of the total concentration of tars;
 carry out a real time measurement, i.e. the device should be capable of providing a measurement every minutes, or at least the occurrence of a measurement has to be compatible with tracking which may be considered at continuous (of the order of one minute) including trace concentrations;
 carry out an on-line measurement of the concentration of tars and at the very least conduct the measurement under temperature and pressure conditions as close as possible to those prevailing in the measurement point in order to limit measurement errors related to an additional pick-up or sampling operation. The question is of avoiding any modification of the tar concentration by a change in value of the temperature and pressure parameters. The temperature of the gas to be measured may be located in the high temperature region (T>800° C.) which is a strong constraint as regards measurement;
 not perturb both upstream and downstream the industrial process for producing gas.

The methods proposed hitherto for determining the tar concentration of a gas are divided into four large families:
 a first family which groups analytical methods based on liquid or gas phase chromatography coupled with a detector. The most frequent detectors in the case of measurement of tars are the flame-ionization detector (FID) and the mass spectrometer. The latter is currently used for analyzing combustion gases of steel works. However the acquisition of such an apparatus, which remains above all a laboratory apparatus, remains expensive and does not always prove to be able to carry out quantitative measurements because of the difficulty in interpreting the spectra and the low repeatability of the measurements. In the absence of a preliminary concentration step, chromatography does not allow continuous measurements to be carried out for low detection thresholds (less than 1 $mg/Nm^3$). The currently used methods for the pre-concentration of traces are solid phase extraction (SPE), and since a few years solid phase micro-extraction (SPME). These techniques consist in the absorption or adsorption of chemical species on a support covered with an absorbent or adsorbent species. This is for example a fibre of molten silica covered with a polymer, which may be for example a liquid polymer such as polydimethylsiloxane (PDMS). This sampling step poses different problems like the representativity of the sample related to the selective character of the absorbent or adsorbent. Moreover, the use of liquid or gas phase chromatography is not very suitable for measuring species for which the molar mass is relatively large (M>400 g/mol). A continuous measurement of the total concentration of tars in a gas can thus not be obtained by chromatography.

a second family which groups so-called <<spectrometric methods>>, which consist in detecting and analyzing a spectrum. This is for example infrared, ultraviolet (UV) or luminescence spectrometry, LIBS (Laser-Induced Breakdown Spectroscopy) technique. The advantage of applying UV absorption which is very close to that of absorption in the infrared, is that steam does not interfere in the UV range. The latter is used for example for detecting polycyclic aromatic hydrocarbons in contaminated soils as mentioned in patent EP0446975 entitled <<Installation of the rapid analysis of tar components and method for such an analysis>>. Patent WO9833058, as for it, relates to a method for on-line analysis of polycyclic hydrocarbons by collecting the aerosols by means of a filter and by submitting the latter to excitation via UV radiation. Next, the question is of comparing the obtained spectral image with various spectra listed in a database. Another currently used technique in the continuous monitoring of combustion gases is FTIR (Fourier Transform InfraRed) infrared spectrometry. Miscellaneous documents mention this technique, such as for example WO2006015660, WO03060480 and U.S. Pat. No. 5,984,998. The literature does not mention a possibility of measuring tars, the currently tracked products being CO, $CO_2$, $O_2$, $H_2$ and $H_2O$. In our case, the presence of steam in the synthesis gas is a source of perturbation in infrared absorption. The FTIR method is qualitative in the sense that it gives information on the nature and the proportion of atomic groups and that only asymmetrical molecules may be measured. Another limitation consists in the determination of mathematical models required for quantifying the measurement. Patent WO030227650 relates to the use of the LIBS (Laser-Induced Breakdown Spectroscopy) technique with view to detecting polycyclic aromatic hydrocarbons (PAHs) and mono-aromatics. This fast method is adapted to the monitoring of PAHs. The LIBS technique consists of vaporizing and ionizing the sampled species as a plasma by means of a laser. However it requires the use of a support on which are present the species to be analyzed. It therefore requires a sampling step and does not allow on-line measurement of the gas.

a third family which groups so-called <<electronic>> methods. We may cite as an example the measurement of organic compounds by means of photo-ionization or flame ionization. The document referenced as: O. Moersch, H. Spliethoff, K. R. G Hein, <<*Tar quantification with a new online analyzing method*>>, *Biomass and Bioenergy*, Volume 18, 2000, pages 79-86, mentions a quasi-continuous method for determining tars by means of two flame ionization detectors. With a first detector it is possible to determine the total amount of hydrocarbons and the second measurement measures the amount of non-condensable hydrocarbons. Both detectors are placed in different points of the same sampling conduit for the gas to be measured and are separated by a filter which has the purpose of trapping the tars by impaction and condensation. One of the limits of the flame ionization technique is the perturbation of the measurement by combustible gases such as $CH_4$, $H_2$ and CO which is a real limitation insofar that synthesis gas is a mixture of CO and $H_2$ and that it also contains methane. Further, the response depends on the oxygen content of the gas to be measured. Finally, knowledge of the composition of the tars as well as of the response factors of various compounds is absolutely necessary for obtaining a quantitative measurement of the total tars. There exist other electronic methods which allow continuous monitoring of tars: these are detectors with electrochemical cells and sensors with semiconductors. An electrochemical cell consists of a membrane letting through the compounds to be analyzed by permeation; on the other side of the membrane is located a liquid electrolyte which, in the presence of the species to be detected, generates an oxidation-reduction reaction at the origin of a measurable electric current. This device is not suitable for a measurement in temperature, further the selectivity of the membrane is not compatible with the sampling of a large number of components, for which the physico-chemical properties vary over a wide range of values. Sensors with semiconductors have similar limitations in terms of resistance to temperature, on the other hand a large number of pollutants may be measured with them. A significant limitation of this device also lies in the fast contamination of the sensitive layer of the semiconductor placed above the substrate. These so-called <<electronic>> methods allow the concentration of tars to be tracked continuously but a quantitative measurement of the totality of the tars present in a gas flow at high temperature cannot be obtained;

a fourth family which groups so-called <<gravimetric>> methods of which a division may be made depending on whether solvents are used or not. The large majority of the methods encountered in the literature involve at least one solvent. They use in a combined way the same physical principles which are: filtration (impaction), condensation, absorption by solvent and extraction (evaporation). Next the question is to evaluate the mass difference of the various elements (filters, cryogenic traps, . . . ) by weighing between the beginning and the end of the measurement. These methods, with an often complex and long experimental procedure, are exclusively suitable for laboratory use. They require a significant sampling time (>30 min) in order to be able to detect low concentrations (less than 1 mg/$Nm^3$) and they do not allow continuous and on-line tracking of the tar content of a hot gas. The work originating from the European <<tar protocol>> project (ENK5 CT 2002-80648) is a reference in the field of analysis and measurement of the tar content in gases from gasification processes. The last version (version 3.3) to date is entitled <<*Guideline for Sampling and Analysis of Tar and Particles in Biomass Producer Gases*>>. With this procedure it is possible to conduct both a quantitative and qualitative measurement of tars present in the gas state and in the solid state per sample. The measurement is conducted by isokinetic sampling for a range of temperatures from 0 to 900° C. and a pressure ranging from 0.6 to 60 bars and this for a tar concentration ranging from 1 to 300 mg/$Nm^3$. This protocol proves to be thus unsuitable for measuring tar traces (<1 mg/$Nm^3$). There exist a large number of procedures derived from this protocol which aim at simplifying the latter. Generally, gravimetric methods prove to be suitable for the measurement of so-called <<heavy>> tars (with more than 3 aromatic rings as regards polycyclic aromatic hydrocarbons (PAHs)) but not very suitable for that of volatile organic compounds. As mentioned above, there also exist gravimetric methods which do not use any solvent such as the one developed by Iowa State University. In the document referenced as: Ming Xu, Robert C. Brown, Glenn Norton, and Jerod Smeenk, <<*Comparison of a Solvent-Free Tar Quantification Method to the International Energy Agency's Tar Measurement Protocol*>>, Center for Sustainable Environmental Technologies, Iowa State University, *Energy & Fuels* 2005, 19, 2509-2513, the authors propose a measurement, the principle of which consists of condensing the organic components in a Santoprene tube maintained at a temperature above that of boiling water (i.e. 105° C.). Santoprene is a material which was selected for its resistance towards the devolatilization phenomenon. The advantage of this method lies in its simplicity but it requires a sampling time of 60 minutes for a gas flow rate of 2 L/min in order to obtain a detection limit of the order of 1 mg/Nm$^3$. The obtained performances are very close to that of the <<tar protocol>> but with this method, it is only possible to measure so-called <<heavy>> tars. This is therefore a relatively long, partial and non-continuous method.

Thus, most methods for measuring tars are above all qualitative and discontinuous, so that they cannot meet an industrial need which is on-line and continuous monitoring of the concentration of tars.

Moreover, very frequently, an additional step for filtering and removing steam is required in order to limit the perturbations of the results of measurement on the one hand and possible degradations of the measurement material on the other hand. The same applies for the presence of oxygen.

Having arrived at this point of the description, mention may further be made of document P. Broutin, F. Ropital, M-F Reyniers, "*Anticoking Coatings for High Temperature Petrochemical Reactors*", *Rev IFP*, Vol. 54 (1999), No 3, pp 375-385: these are coking tests applied to different coatings used in the structure of the reactors. The asymptotic coking rate which corresponds to the contribution of the thermal effect on coking is evaluated by micro-weighing. This method measures by weighing, the affinity of various coatings to form coke by measuring their coking rate, instead of measuring the concentration of traces of tars in a gas. The present invention relates to another measurement and rather utilizes the catalytic effect of the coking on a catalyst.

None of the presented solutions is therefore able to meet the following requirements: a continuous, quantitative, total, and on-line measurement of traces of tars (detection threshold less than one mg/Nm$^3$).

None of the presented devices is able to carry out a measurement of the total concentration of tars continuously with a measurement occurrence of the order of one minute.

Moreover, the presented devices do not measure the whole of the tars, whether they are in a solid phase or in the gas state.

The pursued goal is to carry out a quantitative and continuous measurement of the whole of the tars present in the solid phase or the gas state in a gas flow at a high temperature. Further, the measurement should be representative of the total tar content prevailing in a main conduit in which flows a synthesis gas under given temperature and pressure conditions.

GENERAL DESCRIPTION OF THE INVENTION

The aforementioned objects are achieved by the present invention developed by the inventors. This is a device and a method for continuous measurement of the concentration of tars in a gas, which may be at a high temperature. It comprises a thermogravimetric sub-assembly which may, depending on the case, be combined with a calorimetric measurement, inter alia.

In a general form, the invention relates to a device for continuous measurement of the concentration of tars in a gas, characterized in that it comprises a conduit for sampling a partial flow of the gas and scales to which the sampling conduit leads and from which a body is suspended, used as a catalyst and support for coking of tars, the body being mobile in the gas duct enclosure.

A detrimental phenomenon is thereby used which is the inactivation of catalysts by coke deposit in order to accomplish a measurement in the particular field of continuously monitoring traces of tars in a gas flow.

Various enhancements of the invention are proposed. According to a first of them, a device for adjusting the temperature of the sampled gas is added at the location of the thermogravimetric scales or just upstream, in order to notably establish a determined and often higher temperature at the location of the catalytic body, where coking should be promoted. On the other hand, the remainder of the device, and firstly the sampling conduit, will often be provided with means dedicated to maintaining the temperature of the gas to the value of that prevailing in the main flow, in order to avoid condensation and reactions of the tars. The elements of devices other than the catalytic body will preferably be selected in a material not having much affinity for coke formation, in order not to be fouled and especially to not reduce the concentration of the tars before arrival of the gas at right angles to the catalytic body.

The catalytic body is advantageously a composite of plates or more generally a solid with a large specific-area/specific-gravity ratio in order to provide the largest surface area to catalysis for a determined volume and this while minimizing the weight of the catalytic body, for reasons of sensitivity of the measurement.

The addition of a flow homogenizer upstream from the duct enclosure favorably establishes a uniform flow of gas around the catalytic body and improves the regularity of the measurement. Also, the addition of a flow concentrator in the duct enclosure around the catalytic body directs approximately all the diverted flow onto the catalytic body and improves the efficiency of the catalysis.

With a driver gas injector in the duct enclosure, it is possible to protect the electronic portion of the micro-weighing measurement sub-assembly.

At least one buffer capacity is favorably located on the conduit upstream from the enclosure in order to regulate the diverted flow rate, and to here again improve the accuracy of the measurement. A diaphragm may be located on the conduit downstream from the buffer capacity in order to assist with setting the value of the flow rate crossing the duct cross-section and the catalytic body.

Still advantageously, the scales comprise an oscillating symmetrical beam at one end of which the catalytic body is suspended and at an opposite end of which a non-catalytic body for coking the tars is suspended, the catalytic body and the non-catalytic body having identical weights.

As this form of scales carries out a differential measurement, only one of the bodies becoming heavier during the measurement, it is particular accurate due to its symmetry. It is further advantageous if the non-catalytic body is mounted so as to be mobile in a second enclosure identical with that of the catalytic body, in order to contribute to regularity of measurement by symmetry of flow. A pressure equalizer between both enclosures further adds to this regulation.

If the rod is suspended from the beam of the scales by magnetic coupling, the enclosure including the catalytic body is vertical and comprises an aperture for recovering the catalytic body at one bottom, whereby the replacement of the catalyst body from one measurement to the other is much facilitated. In order to reinforce this effect, a member may be added to the device for changing the mobile catalytic body between the aperture of the bottom of the duct section and a station for changing the catalytic body.

According to an optional but particularly useful element of the invention, either an auxiliary sensor for measuring the concentration of a gas produced during coking downstream from the catalytic body and located on a gas discharge conduit, or further, preferably, an auxiliary calorimetric sensor of the catalytic body are added. This use of colorimetry is possible since the catalytic body gradually changes color as deposition of coke develops. By coupling the gravimetric measurement with a calorimetric measurement, after having calibrated the calorimetric measurement by means of the gravimetric measurement, it is possible to use the calorimetric measurement alone, if necessary since with its very low detection threshold, less than that of the scales, the latter may be replaced for very low concentrations of tars or for a preliminary step of measurement.

Advantageously, the calorimetric sensor is designed so as to conduct differential measurements on the catalytic body and on the non-catalytic body when the latter exists.

The measurement may be improved by a flowmeter located on the diverted conduit.

An important aspect to be considered is the simultaneous frequent presence of tars in the gas phase or in the solid phase. The preceding method, as described up to now, gives preference to detection of tars in the gas phase, the latter being predominant or even exclusive in many applications, especially at a relatively high temperature of the gases. However an auxiliary of the device allows measurement of the concentration of the tars in the solid phase.

Especially in this situation, it is indicated to position upstream from the sampling conduit, a filter retaining the solid particles in order to only measure the tars in the gas phase in the main device.

The auxiliary device for measuring tars in the solid phase may comprise a trap for solid particles which may be weighed.

A cyclone for sorting solid particles may be added in order to send towards the solid particle trap only the particles which may be considered as tars.

The invention further relates to a method for continuous measurement of the concentration of tars in a gas, characterized in that it consists of sampling a partial flow of the gas and of directing this flow towards a body used as a catalyst and support for coking the tars. There is the possibility of adjusting the temperature of this flow in order to promote coking.

As a reminder, weighing is either continuous in the strict sense or else it is at least carried out at close intervals, of the order of one minute or less, which most prior devices and methods do not allow.

It should be emphasized that it is the catalytic aspect of coking which is preferably utilized in the invention, while coking is especially assimilated to cracking of thermal nature. The catalytic phenomenon especially operates during the formation of the first layer of deposit which is generally carried out by adsorption of the heavy hydrocarbon compounds making up the coke, while the thermal coking phenomenon then becomes generally predominant. The invention will therefore be more particularly useful for measuring low concentrations of tars. The catalyst material for the coking will be selected by its nature, its shape and making, so that the catalytic effect will be larger than the thermal effect in the targeted temperature range, generally from 200 to 1,200° C.

As this has been mentioned, the basis method may be enriched with an additional measurement of the concentration of the tars in the solid phase consisting of trapping the solid tars on a support.

The main measurement by micro-weighing may be completed by auxiliary measurements based on color variations of the catalytic body or on concentrations of gas stemming from the coking and notably of dihydrogen gas, since the formation of coke is generally accompanied by dehydrogenation of tar compounds.

A last aspect which characterizes the invention is the selection of the catalytic body (nature, composition, shaping, geometry . . . ). It depends of four fundamental parameters which are:
the catalytic properties of the material;
the $$\frac{Specific\_surface\_area}{Specific\_gravity}$$

ratio which should be sufficiently large in order to have a measurement as accurate and as representative as possible;
a material for which methane does not coke or only very little;
a color and shape which are compatible with a colorimetric measurement.

The whole of these parameters cannot always be optimized simultaneously, which requires a compromise in order to globally optimize the measurement according to:
the targeted measurement range;
the nature of the applied tars;
the operating conditions, etc.
Exemplary embodiments will be proposed later on.

SHORT DESCRIPTION OF THE DRAWINGS

The invention will be understood upon reading the detailed description which follows of the embodiments of the invention, provided as an illustration and by no means as a limitation, with reference to the appended drawings, wherein.

DETAILED DISCUSSION OF PARTICULAR EMBODIMENTS

Figure 1:
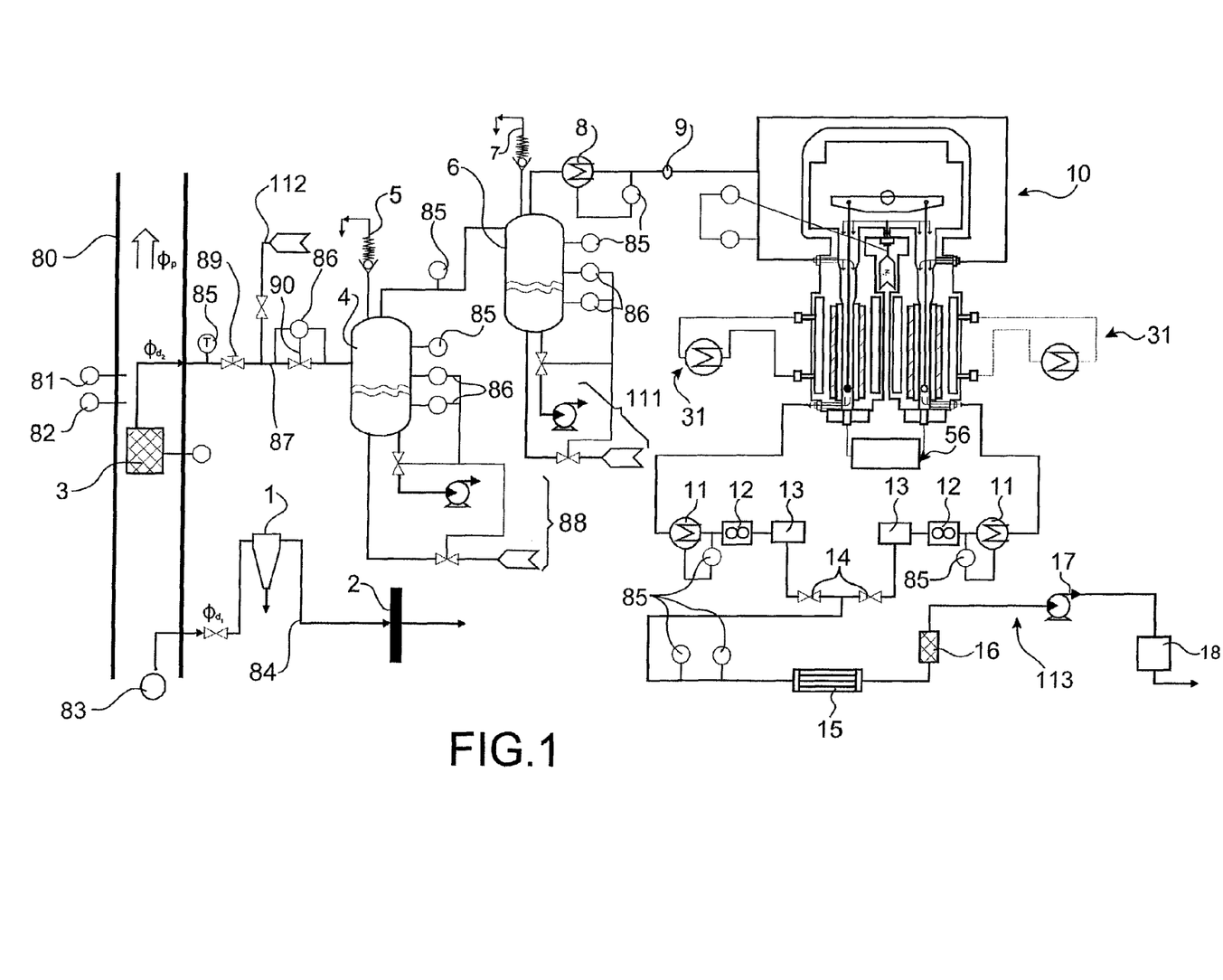
FIG. 1 schematically illustrates a device and a method according to the invention, the goal of which is continuous measurement of tars in the gas and solid state contained in a gas flow in temperature.

Referring first of all to FIG. 1, a device dedicated to the measurement of tars by micro-weighing and/or colorimetry is schematically illustrated.

The gas mixture to be analyzed flows inside a main conduit 80 in stainless steel, for example in AISI 310 or AISI 316. Also alloys based on nickel and chromium (for example Inconel) are currently used as a constitutive material of conduits which may withstand temperatures of 1,200° C. and beyond and have the advantage of having a very small catalytic effect for the coking phenomenon, which allows the deposit of coke or soots to be limited on the internal surfaces of ducts. Said conduit 80 comprises means 81 and 82 allowing continuous measurement of the pressure $P_p$ and the temperature $T_p$ which prevail inside it. The nature and the composition of the gas mixture vary according to the contemplated application. For example, in the case of synthesis gas obtained by gasification of biomass or waste, the species present in majority are CO et $H_2$, both of these compounds form the gas matrix. To a lesser extent, gases are found such as $CO_2$, $CH_4$, $H_2O$ and tars. In the case when the synthesis gas would be intended for producing synthetic fuel, the gas flow upstream from the Fischer-Tropsch process is at a temperature of about 300° C. and at a pressure which may range up to 30 bars.

As illustrated in FIG. 1, a portion of the main flux $\phi_p$ is diverted towards two sampling devices and gives rise to secondary flows $\phi_{d1}$ and $\phi_{d2}$. Actually the global measurement system comprises two devices, the first of which is assigned to discontinuous measurement of the tars in the solid phase and the second to continuous measurement of the tars in the gas state. It is this second device for continuous measurement of the tars in the gas state which is the subject of the invention and which will be mainly described: the first device is optional and is a simple auxiliary intended to complete the measurement.

In order to limit the perturbation of the main flow $\phi_p$ and also in a concern for saving synthesis gas, the sample flow $\phi_d = \phi_{d1} + \phi_{d2}$ satisfies the following relationship:

$$\frac{\phi_d}{\phi_p} < 1\%$$

In the case when the whole of the tars present in the main flow $\phi_p$ are in the gas phase (for example for temperatures above 350° C.), only the first device is used for checking for the absence of solid tars.

The first device, assigned to the measurement of tars in the solid phase, comprises an isokinetic sampling device 83 according to the ISO 9096 and/or ISO 2066 standards. The isokinetic sampling 83 is connected through metal stainless steel conduits 84 to a particle sorting unit such as for example a cyclone 1 or a set of cyclones which perform the separation between the particles with a size larger than a few μm, notably coal or "char" particles, byproducts of pyrolysis of the biomass, and the particles with more modest size such as soots which originate from polycondensation of the tars. Said soots are then collected by impaction on a filtering medium 2 in order to be weighed in a second phase. The whole of the conduits of this device is heat-insulated and maintained at the temperature $T_p$ of the main conduit in order to avoid condensation of the tars present in the gas state in the main flow.

The second device intended for continuous measurement of tar gases consists of three large sub-assemblies which are:
- a system for sampling, treating and conveying the gases (3, 4, 5, 6, 7, 8 and 9);
- thermogravimetric scales (10) adapted to the case of our application which is the continuous measurement of the concentration of tars in a gas flow in temperature via the monitoring of the tar coking phenomenon (conversion of tars into a carbonaceous load), by micro-weighing;
- an analysis system coupled to micro-weighing involving according to the desired application an optical colorimetry measurement system, an $H_2$ analyzer or a $CO_2$ analyzer.

The first two sub-assembles are absolutely necessary for properly carrying out the invention, the third improves the results by corroborating them or compensating for the second sub-assembly in the case of extremely low concentrations of tars.

The second device is located downstream from the first on the main conduit 80 in order not to perturb it.

First Sub-Assembly

The system for sampling, treating and conveying the gases is heat-insulated and maintained at temperature $T_p$ in order to avoid creation of <<cold areas>> which would promote condensation of the tars. The question is also to convey the gas to be analyzed up to the thermogravimetric scales 10 under temperature and pressure conditions as close as possible to those prevailing in the main conduit 80 in order to avoid condensations and reactions of the tars. The question is therefore to have a measurement of the concentration of gas tars which is as representative as possible of the gas tar concentration in the main conduit 80. Maintaining the temperature of the conduits and of various other elements (for example buffer volumes 4 and 6 described later on) may be accomplished by means of an electric heating device or by circulation of hot nitrogen around said conduits and other members for treating and conveying the gas to be analyzed.

The system for sampling, treating and conveying the gases comprises means 85 and 86 with which temperature and pressure may be measured in various points.

The sampling system comprises a frit 3 which may be metal. The constitutive material of the frit 3 should be cleverly selected in order to limit the catalytic effect leading to the formation of coke and therefore to destruction of the tars; this for example may be a material formed on the basis of silicon carbide SiC. The frit 3 may just as well and this in a non-limiting way be in quartz, ceramic or glass fiber. Said frit 3 is maintained in temperature by means of a heating device in order to avoid condensation of tar compounds notably promoted by the pressure loss which it induces. The frit 3 is used as a filter for the solid particles but allows a portion of the gas flow to flow in a sampling conduit 87 leading from the main conduit 80 to the thermogravimetric scales 10 and bearing various pieces of equipment which will now be described gradually. The sampling conduit 87 is heat-insulated and maintained at the temperature $T_p$ of the flow, prevailing in the main conduit 80

A cut-off valve 89, a purge conduit 112 and an expansion valve 90 are placed between the frit 3 and a first buffer volume 4.

The first buffer volume 4 is a capacity equipped with means with which the pressure and temperature may be measured in it. It comprises a nitrogen filling and emptying system 88 with which, associated with a pressure control device, it is possible to perform smoothing of the flow rate and pressure of the gas to be analyzed. A safety valve 5 is placed at the top of the buffer volume 4 in order to avoid possible overpressures and to guarantee the safety of the device.

A second buffer volume 6 with slower dynamics than that of the first buffer volume 4 performs finer smoothing of the flow and of the pressure; it follows the first buffer volume 4 and also comprises a nitrogen filling and emptying system 111 and a safety valve 7.

A heat exchanger 8 is placed downstream from the second buffer volume 6 in order to adapt the temperature of the gas to be analyzed before introducing the latter in two thermostatted enclosures of the thermogravimetric scales 10. In the case when the temperature inside the thermogravimetric scales 10 should be much higher than the temperature $T_p$ inside the main conduit, the exchanger 8 will form an area for preheating the gas to be analyzed in order to obtain better efficiency of the thermogravimetric device; the temperature in the thermostatted enclosures of the thermogravimetric scales 10 is determined for an optimum coking rate of tars by a catalytic effect.

A diaphragm 9 is positioned before joining the sampling conduit 87 to the thermogravimetric scales 10 in order to limit the flow rate.

Second Sub-Assembly

First Embodiment

Figure 2:
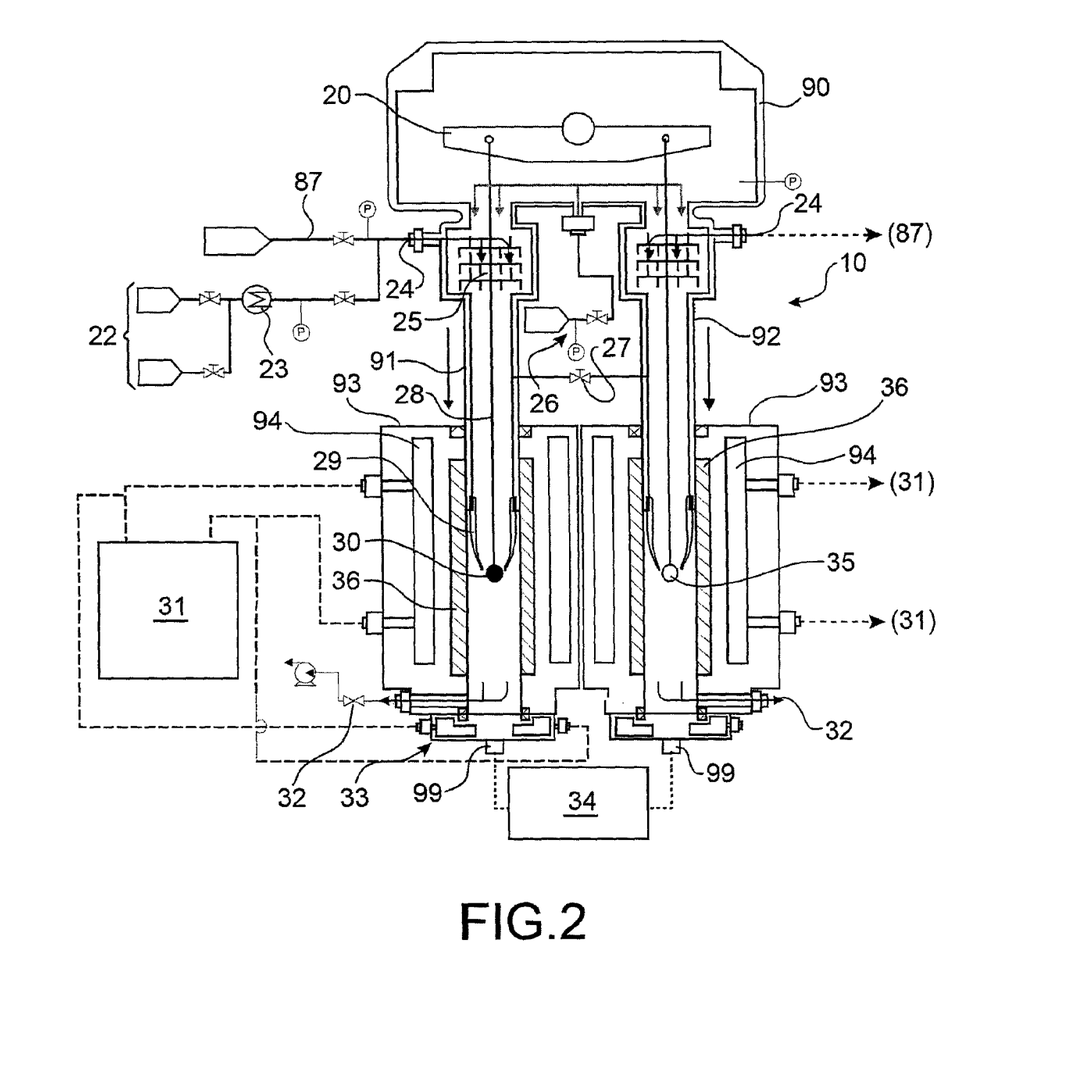
FIG. 2 is an exemplary embodiment of the thermogravimetric sub-assembly allowing continuous tracking of the tars by micro-weighing.

The thermogravimetric sub-system equipped with the thermogravimetric scales 10 will now be described with reference to FIGS. 2 and 3. FIG. 2 schematically illustrates a first embodiment of the thermogravimetric scales 10. The different embodiments shown hereafter all have the specificity of having two ovens with thermostatted enclosures, these are so-called scales with a <<symmetrical configuration>>. Thermogravimetric scales having a single thermostatted enclosure, without their being excluded from the invention, would require after each measurement the carrying out of a blank measurement in order to get rid of various sources of error of the measurement such as hydrostatic buoyancy and flow rate fluctuations for example.

Figure 5:
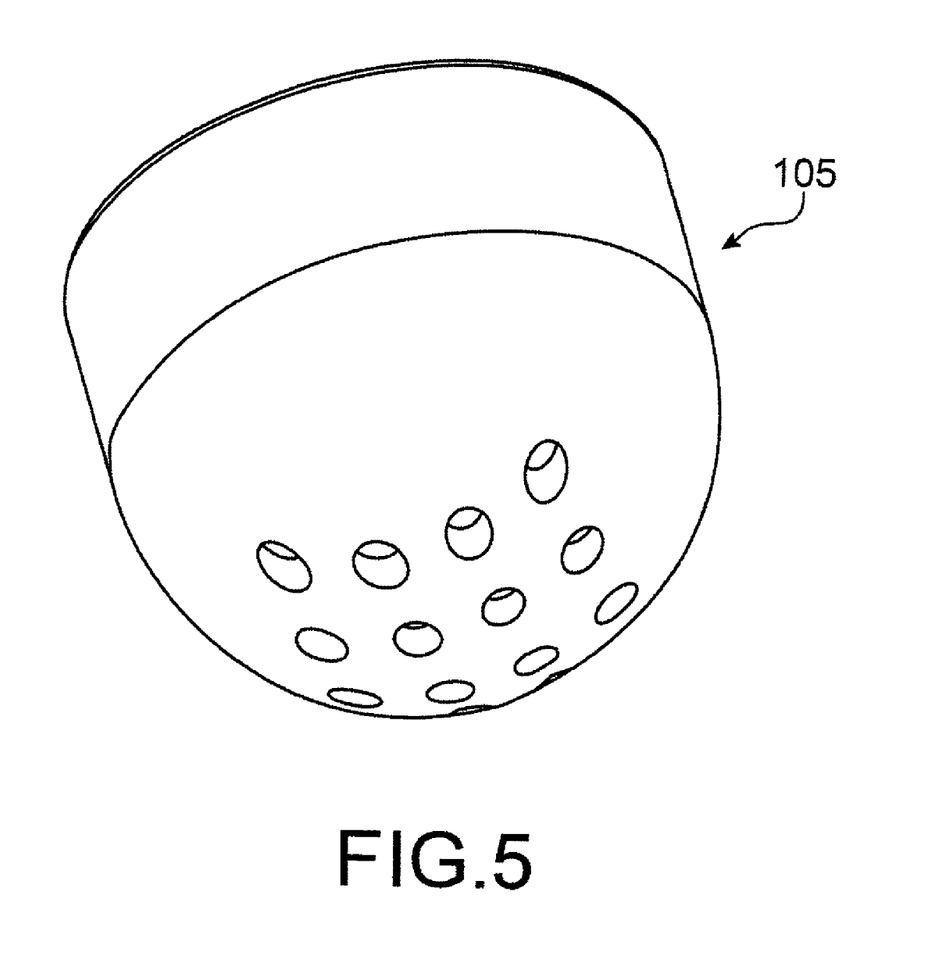
FIG. 5 illustrates a micro-perforated boat which may be suspended from the rod of the thermogravimetric scales and which may contain the coking material 30.

The thermogravimetric scales 10 comprise:
- an enclosure consisting of several portions, an upper enclosure 90 of which housing a beam 20 and a pair of lower and vertically extended thermostatted enclosures 91 and 92 extending upwards up to the upper enclosure 90 and downwards as far as an accessibility plug 33;
- a system 26 for supplying protective gas, for example He or $N_2$, in order to protect an electronic weighing device by blowing an inert gas into the upper enclosure 90;
- a connection of the thermostatted enclosures 91 and 92 through inlet orifices 24 to the sampling conduit 87 (having branched off) with which the gas to be analyzed may be conveyed to the thermogravimetric scales 10 by having it cover the thermostatted enclosures 91 and 92 from top to bottom, so that it is channelled therein;
- a purge gas supply system 22, including a heating system 23 with which the lowering of temperature may be limited in the thermostatted enclosures 91 and 92 during the purge of the system. The purge gas may for example be an inert gas, or air;
- a Joule effect heating system 36 of tubular shape including at least partly each of the thermostatted enclosures 91 and 92;
- a device 25 for homogenizing the temperature and flow of the gas to be analyzed, positioned at the inlet of each of the thermostatted enclosures 91 and 92;
- a flow concentrator device 29 which acts by restricting the section of flow provided to the gas;
- a cooling device 31 applying a liquid coolant, for example water, with which both thermostatted enclosures 91 and 92 may be cooled at the periphery and seal gaskets at the lower and upper portions of the thermostatted enclosures 91 and 92;
- a system for uniformizing the pressures 27 between both thermostatted enclosures 91 and 92;
- an accessibility plug 33 at the bottom of each of the thermostatted enclosures 91 and 92 in order to limit the temperature drop in the thermostatted enclosures 91 and 92 while allowing access to them for operations of replacement of a catalytic body 30 and of a non-catalytic body 35 to be described;
- a micro-weighing measurement device with a resolution of less than one microgram, comprising an electronic and mechanical device. The mechanical device comprises a symmetrical beam 20 housed in the upper enclosure 90 and two rods 28 suspended from the beam 20 and housed in the thermostatted enclosures 91 and 92, respectively. The electronic device is not illustrated, as it is known per se, and measures the rotation of the axis of the beam 20;
- a catalytic body 30 both a support and catalyst for the coking reaction with its attachment system to one of the rods 28, which may be, depending on the case, a perforated boat (105 in FIG. 5), a supporting ring or any other shape allowing the rod 28 to be firmly attached to the catalytic body 30. The catalytic body 30 is suspended at the height of the flow concentrator 29 of the thermostatted enclosure 91;
- a non-catalytic body 35 of the same weight as the catalytic body 30 is suspended from the other rod 28 in order to balance the beam 20, itself also at the height of the flow concentrator 29;
- a heating assembly comprising tubular ovens 36 surrounding the thermostatted enclosures 91 and 92 at the bodies 30 and 35, a heat-insulating coating 93 surrounding the thermostatted enclosures 91 and 92 and the tubular ovens 36 and heat exchangers 94 placed in the heat-insulating coating connected to a thermostatted bath of the cooling system 31 in order to maintain the assembly at a constant temperature;
- finally, discharge orifices 32 at the bottom of the thermostatted enclosures 91 and 92, through which the gas to be analyzed escapes from the latter in order to flow into a discharge conduit 113 (branching off into two branches close to the thermogravimetric scales in order to lead into each of the thermostatted enclosures 91 and 92).

Figure 4:
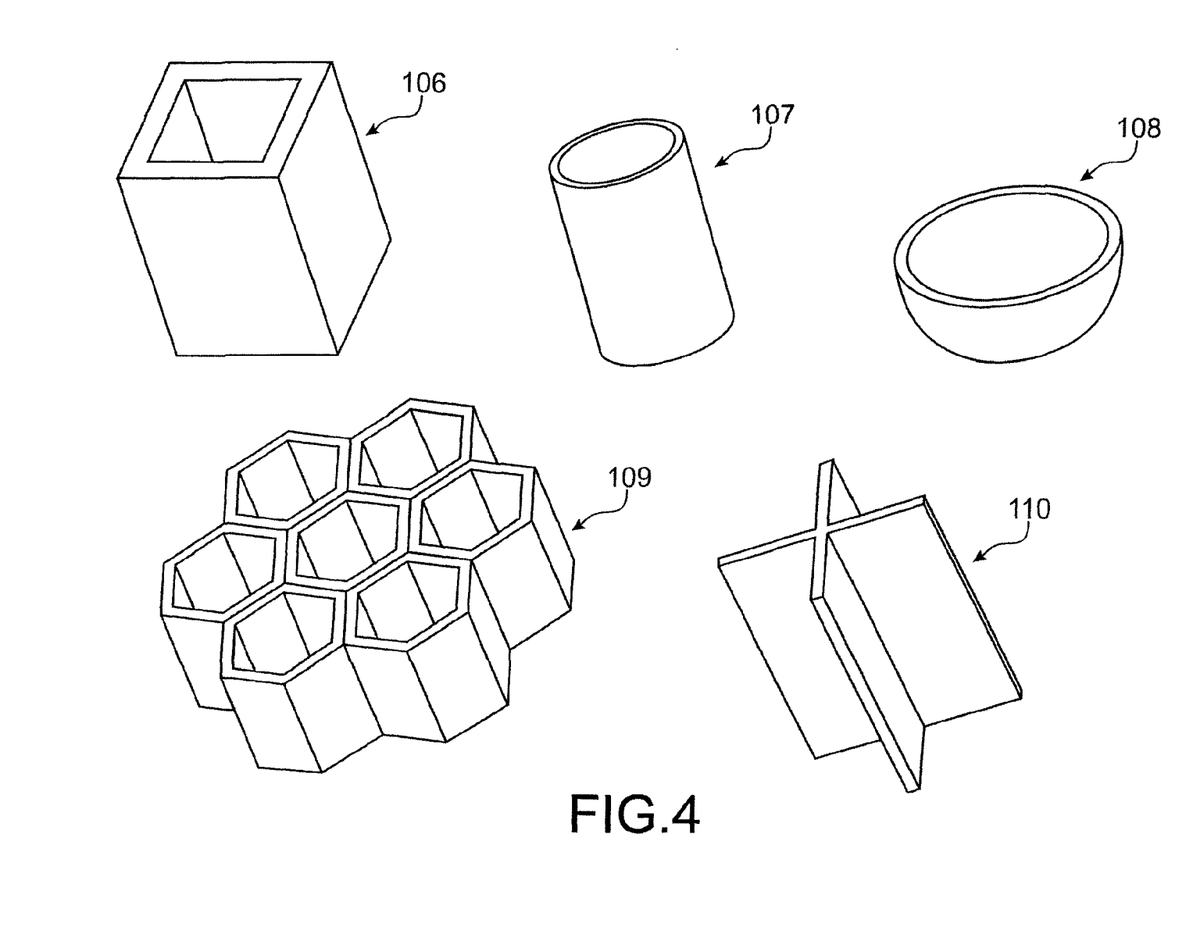
FIG. 4 illustrates different shapes for the catalytic body, support of coking.

The catalytic body 30 may for example be activated alumina, zeolite or even active coal. Materials of a pale color should be preferred in order to be able to couple the micro-weighing measurement to a calorimetric measurement. The shape of the catalytic body 30, illustrated by examples in FIG. 4, is fundamental because it conditions the representativity and accuracy of the measurement.

For this purpose, the use of different shapes and masses may be contemplated depending on the content of tars in the gas to be analyzed and/or depending on the need or not for coupling to a calorimetric measurement. The targeted measurement range between 0.1 mg/Nm$^3$ and 100 mg/Nm$^3$ of tar content in the gas, may be divided into ranges as mentioned below:

measurement range 1: from 0.1 to 1 mg/Nm$^3$;
  measurement range 2: from 1 to 10 mg/Nm$^3$;
  measurement range 3: from 10 to 100 mg/Nm$^3$.

For measurement accuracy questions, the mass of formed coke $m_{coke}$ satisfies the following condition:

$$\frac{m_{coke}}{m_{boat+alumina}} > 1\%$$

where $m_{boat+alumina}$ represents the sum of the mass of the boat and that of the coking material (for example alumina here).

The mass of formed coke is given by the following expression:

$$m_{coke} = \overline{V_{coking}[\Delta t]} \times \Delta t$$

wherein $\Delta t$ represents the duration of the measurement expressed in minutes, $\overline{V_{coking}[\Delta t]}$ illustrates the average coking rate over $\Delta t$ expressed in mg/min.

It should be noted that $\Delta t$ is of the order of magnitude of one minute.

The shape of the catalytic body may be, and this in a non-limiting way, a plate, a hollow cone, a bead, etc. or a combination of such shapes, and notably combinations of plates with any shape. A tube with a square cross-section 106, a round tube 107, a cup 108, a honeycomb 109 and a cross-shaped member 110 are found in the examples of FIG. 4. It is important than the shape used maximizes the coking rate. The coking rate $\tau_{coking}$, an adimensional quantity, is given by the expression below:

$$\tau_{coking} = \frac{m_{coke}}{m_{tars}}$$

wherein $m_{coke}$ represents the mass of coke formed during $\Delta t$, $m_{tars}$ represents the mass of tars contained in the flow for a duration $\Delta t$.

The coking rate $\tau_{coking}$ at a given instant mainly depends on:

the operating conditions such as temperature and pressure;
the material used as support and catalyst for the formation and deposit of coke (nature, shaping, hydrocarbon species overlapping rate . . . );
the concentration of tars in the gas to be analyzed;
the flow properties, such as velocity, gas flow, the kind of state of flow (a turbulent state promotes the coking phenomenon), efficiency of the gas flow convergence device 29.

The mass of tars $m_{tars}$ contained in the gas passing through the measurement device during $\Delta t$ is given by the following expression:

$$m_{tars} = [tars]_m \times Q_m \times \Delta t$$

wherein $m_{tars}$ represents the mass of tars contained in the flow for a duration $\Delta t$, expressed in milligrams;

$Q_m$ represents the gas volume flow rate expressed in $Nm^3/min$;

$[tars]_m$ represents the mass concentration of tars expressed in $mg/N^3$;

$\Delta t$ represents the measurement duration expressed in minutes.

The coking rate $\tau_{coking}$ is a quantity which relates the measured quantity $\overline{V_{coking}}$ to the unknown $[tars]_m$:

$$\tau_{coking} = \frac{m_{coke}}{m_{tars}} = \frac{\overline{V_{coking}}}{[tars]_m \times Q_m}$$

Therefore the coking rate is an indicator of the performance and of the representativity of the measurement.

For a given catalytic body 30 and a given mass of the latter, its surface area available because of its shape and of its manufacturing method, has to be maximized. A specific-surface-area/specific-gravity ratio larger than 50 $m^5/kg^2$ is recommended.

Second Sub-Assembly

Second Embodiment

Figure 3:
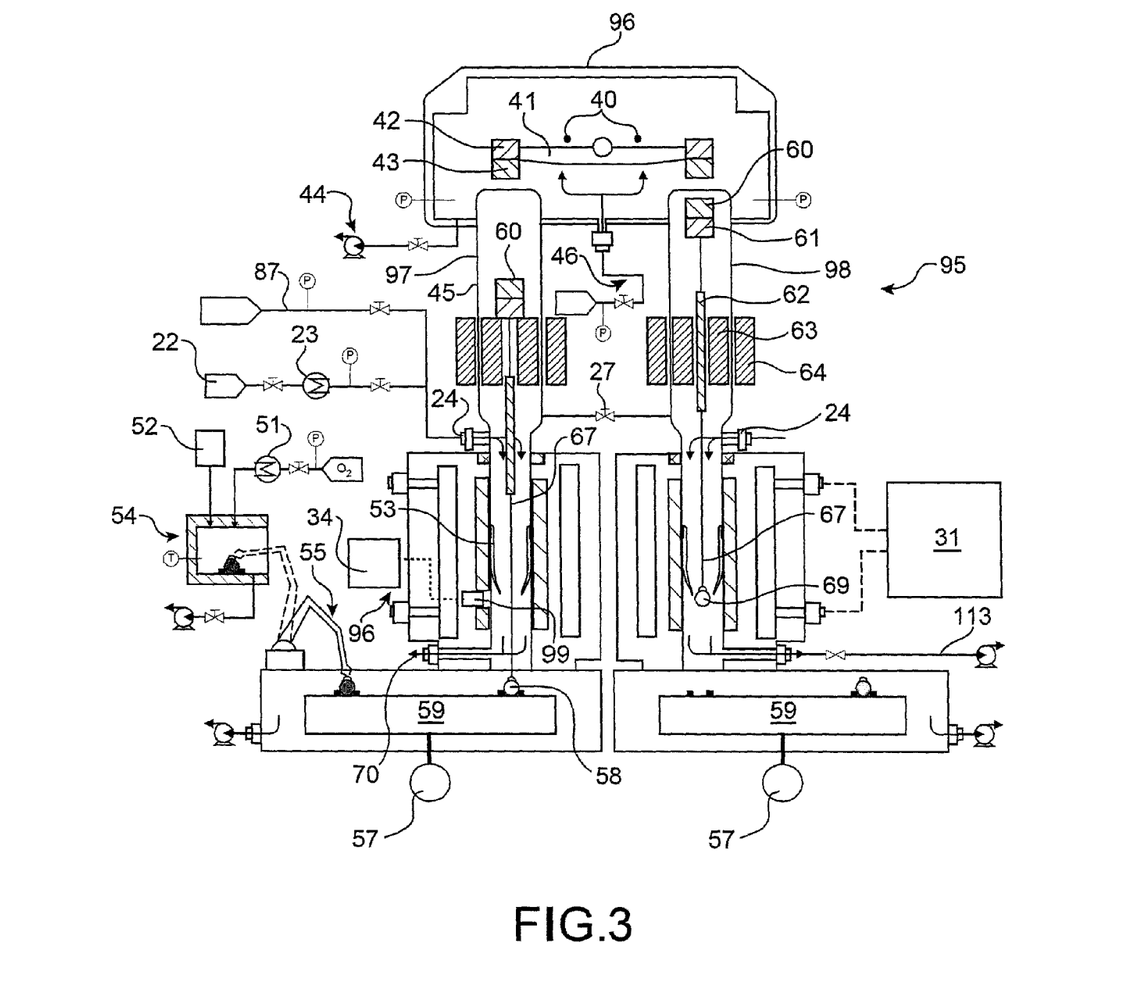
FIG. 3 is another exemplary embodiment of the thermogravimetric sub-assembly. These are thermogravimetric scales with magnetic suspension which were adapted to the case of our application.

FIG. 3 schematically illustrates a second embodiment of thermogravimetric scales. These are thermogravimetric scales 95 with a magnetic suspension which have the advantage of performing physical decoupling between the electronic portion and the mechanical and magnetic portion of the apparatus. This allows pressure operation and absence of any dilution phenomenon via the mixture which occurs between the gas to be analyzed and the protective gas of the electronic portion; a dilution may be limiting in the case of detection of low concentrations of tars. An upper enclosure 96 containing the electronic portion (not shown) and a beam 41 with at both of its ends a magnet 43 and its support 42 continuously receives a nitrogen flow injected in its middle by a pressure supply system 46. Abutments 40 limit the movements of the beam 41, notably when the suspension rods (67 here) are disconnected as this will be described later on. The inerting gas is continuously extracted from the upper enclosure 96, and then recycled in it, by means of a pump 44. Said upper enclosure 96 is physically separated from the thermostatted enclosures 97 and 98, locations of the gas flow to be analyzed and of the measurement, by ceramic walls 45 which also separate the latter from the outside. On either side of these walls 45, already mentioned magnets 43 and other magnets 60 and their supports 61 are found, which allow the rods 67 to be magnetically suspended from the thermogravimetric scales 95, from which are suspended at their other end a catalytic body 58 for coking and a non-catalytic body 69, respectively. With a radial magnetic suspension system, it is possible to ensure upward and downward motion of the rods 67 which have been illustrated in a low configuration in the left thermostatted lower enclosure 97 and in the high so-called "measurement" position in the right thermostatted lower enclosure 98 in FIG. 3. The radial suspension comprises magnets 62 attached to the rod 67, magnetic cores 63 attached in the enclosures 97 and 98 and coils 64 outside the enclosures 97 and 98, capable of exciting the magnetic cores 63 in order to form linear motors with the magnets 62 and to lower the rods 67 towards the bottom of the device or to raise them until re-establishment of the attraction at a distance between the pairs of magnets 43 and 60. When the attraction is established, the rods 67 and the elements which are attached to them exert a force corresponding to their weight on the beam 41 in spite of the lack of contact. The input orifice 24 of the gas to be analyzed in each lower enclosure 97 or 98 is placed under all these magnets and components 60 and 64.

The flow of the gas is directed onto the catalytic body 58 and the non-catalytic body 69 by flow concentrator devices 53 before escaping from the thermostatted enclosures 97 and 98 through discharge orifices 70.

Automated carrousel mechanical devices 59 rotating on motors 57, for example close to the one mentioned in document U.S. Pat. No. 6,468,475 B1, allow the catalytic body 58 and the non-catalytic body 69 to be loaded and unloaded automatically from either one of the two lower enclosures 97 and 98 of the thermogravimetric scales 95 with a symmetric configuration.

For the remainder, the elements are similar to those of the embodiment presented earlier and illustrated in FIG. 2.

Third Sub-Assembly

The analysis device coupled with micro-weighing will now be described with reference to FIGS. 1, 2 and 3 which involve depending on the desired application an optical measurement system by colorimetry 56, a $H_2$ analyzer 18, a $CO_2$ analyzer 52.

Said optical system for measurement by colorimetry comprises an optical device 99 and a module for acquiring and treating images 34. With this device, it is possible to carry out a continuous measurement in the sense that the occurrence (of the order of one minute) of the measurement is sufficient for on-line monitoring of the tar concentration. Said optical calorimetric measurement system 56 allows measurements to be conducted for concentrations of tars for which it is not possible to carry out a measurement by micro-weighing. The idea is to observe the change in color of the catalytic body 30 support and catalyst of the coking reaction which occurs when the first layer of coke is adsorbed. Beyond this first layer, growth of the deposited coke layer continues but the latter then occurs under the effect of a thermal reaction and no longer both catalytically and thermally.

In the embodiment of FIG. 2, the calorimetric device compares the hues of the bodies 30 and 35, the optical devices 99 being placed at the bottom of the accessibility plugs 33 and oriented vertically in the axis of the duct sections; in the embodiment of FIG. 3, where carrousels 59 occupy the bottom of the duct section, an optical device 99 is oriented horizontally, crossing the heat-insulated wall 93, at the height of the catalytic body 58 when it is found in the measurement position, just below the flow concentrator 53. In the embodiment of FIG. 3, an alternative has moreover been illustrated according to which the measurement is not differential and no optical device 99 is oriented towards the non-catalytic body 69. This however is not specific to the respective embodiments and converse arrangements may be selected for each of them.

As this has been mentioned, the calorimetric device is first calibrated during a series of preliminary measurements where the results obtained on the gradual darkening of the catalytic body 30 or 58 are correlated with the weight increase of the latter, measured by the thermogravimetric scales 10 or 95; and the calorimetric device is then capable of conducting standalone measurements, particularly appreciated when the gravimetric measurement does not provide sufficient accuracy when the weight of the coke deposited on the catalytic bodies 30 or 58 is still too small, or when the tar content is very low; it may also give measurements used for corroborating those obtained by gravimetry.

All this applies to the following devices for analyzing gases stemming from coking or from subsequent combustion of the formed coke.

Let us refer back to FIG. 1. An $H_2$ analyzer 18 is placed downstream from the thermogravimetric device 10 for tracking coking. This may for example be an analyzer of the paramagnetic type. The idea is to obtain additional information on the decomposition of tars since at the formation of coke, the tar compounds are dehydrogenated. Such an analyzer may be used in the case of an application where the gas matrix contains no or even very little hydrogen. Between the outlet of the gases from the thermogravimetric scales 10 and the $H_2$ analyzer 18, the following elements on the discharge conduit 113 are positioned in the indicated order:

an exchanger 11 with which the temperature of the gases exiting the thermogravimetric scales 10 may be lowered;

measurement means such as a flowmeter 12 and a volumetric counter 13;

a micrometric valve 14 allowing adjustment of the flow passing through the thermostatic enclosures; and after confluence of both branches of the discharge conduit 113;

a condenser 15 with which the different condensable species such as tars which have not been coked or steamed may be condensed;

an absorbent 16, for example in silica gel, with which the condensables may be trapped;

a pump 17 allowing adjustment of the flow of the gas to be analyzed.

In the embodiment of FIG. 3, a $CO_2$ analyzer 52 analyzes the gases present inside a thermostatted oven 54 in which the coke formed at the surface of the catalytic body 30 is burned by adding oxygen arriving from a conduit equipped with a heat exchanger 52 once the used catalytic body has been removed by the device of the carrousel 59. The idea is to evaluate the amount of formed coke. For this, one has to make sure that the thermostatted oven 54 is free of any trace of $CO_2$ before burning the deposited coke by combustion. The amount of $CO_2$ emitted during the combustion of the coke is measured and correlated with the amount of the latter. An automated mechanical device such as for example an automated jointed arm 55 carries out the loading and unloading of the sample between the carrousel 59 and the thermostatted oven. After combustion of the coke by adding oxygen, it is possible to reuse the catalytic body 30 for a limited number of times. The added oxygen is supplied by a supply system comprising heating means 51.

Operation

The operation of the gas sampling, treating and conveying system (1,2,3,4,5,6,7,8 and 9) will now be described with reference to FIG. 1.

During normal operation, a portion of the main flow $\phi_P$ is sampled at the isokinetic sampling device 83. The cut-off valve is open and lets through a primary sampled flow $\phi_{d1}$ which crosses the cyclone 1 where separation is carried out between the coal (or "char") particles, byproducts of the carbon-rich biomass, and the condensed tars. The tars are then conveyed in the conduits maintained at temperature $T_p$ towards a filtering medium 2, where by impaction the already condensed tars are trapped. The temperature of the main conduit $T_p$, above 300° C., limits condensation of the gas tars at the filtering medium 2. Downstream from the isokinetic sampling device 83, a portion of the main flow $\phi_p$ is sampled as a secondary sampled flow $\phi_{d2}$. The particles are trapped by the frit 3 maintained at temperature $T_p$. The intermittent operation of a pressurized nitrogen supply at the frit 3 avoids fouling of the latter. The cut-off valve 89 lets through the flux $\phi_{d2}$, the pressure of the sampled gas is modified by an expansion valve 90 positioned upstream from the first buffer volume 4. The changes in pressure recorded in the first buffer volume 4 are regulated by the volumetric expansion of the lower portion of the first buffer volume 4, separated from the gas to be analyzed by a membrane. Negative or positive expansion of the low portion is respectively controlled by increasing or reducing the nitrogen pressure. In the case of overpressure in the first buffer volume 4 (a pressure above the set pressure of the safety valve 5), the safety valve 5 opens and lets through a portion of the flow towards a discharge circuit. At the exit of the first buffer volume 4, the flow is conveyed towards the second buffer volume 6, the operation of which is identical with that of the first buffer volume 4; only the operation dynamics differs, which in the case of the second buffer volume 6 is lower than that of the first buffer volume 4. At the exit of the second buffer volume 6, the heat exchanger 8 allows the gas flow temperature to be adapted before admitting it into the interior of the thermostatted enclosure of the thermogravimetric scales 10. The temperature prevailing in the thermostatted enclosure is an optimum between the coking rate of the tars and phenomena such as thermal cracking and vapo-reforming of the coke due to a high temperature and to the presence of steam in the gas matrix. With the diaphragm 9, the flow rate and the pressure fluctuations present in the gas sampling, conveying and treatment system may be mitigated.

The operation of the thermogravimetric scales 10 will now be described with reference to FIG. 2.

Figure 6:
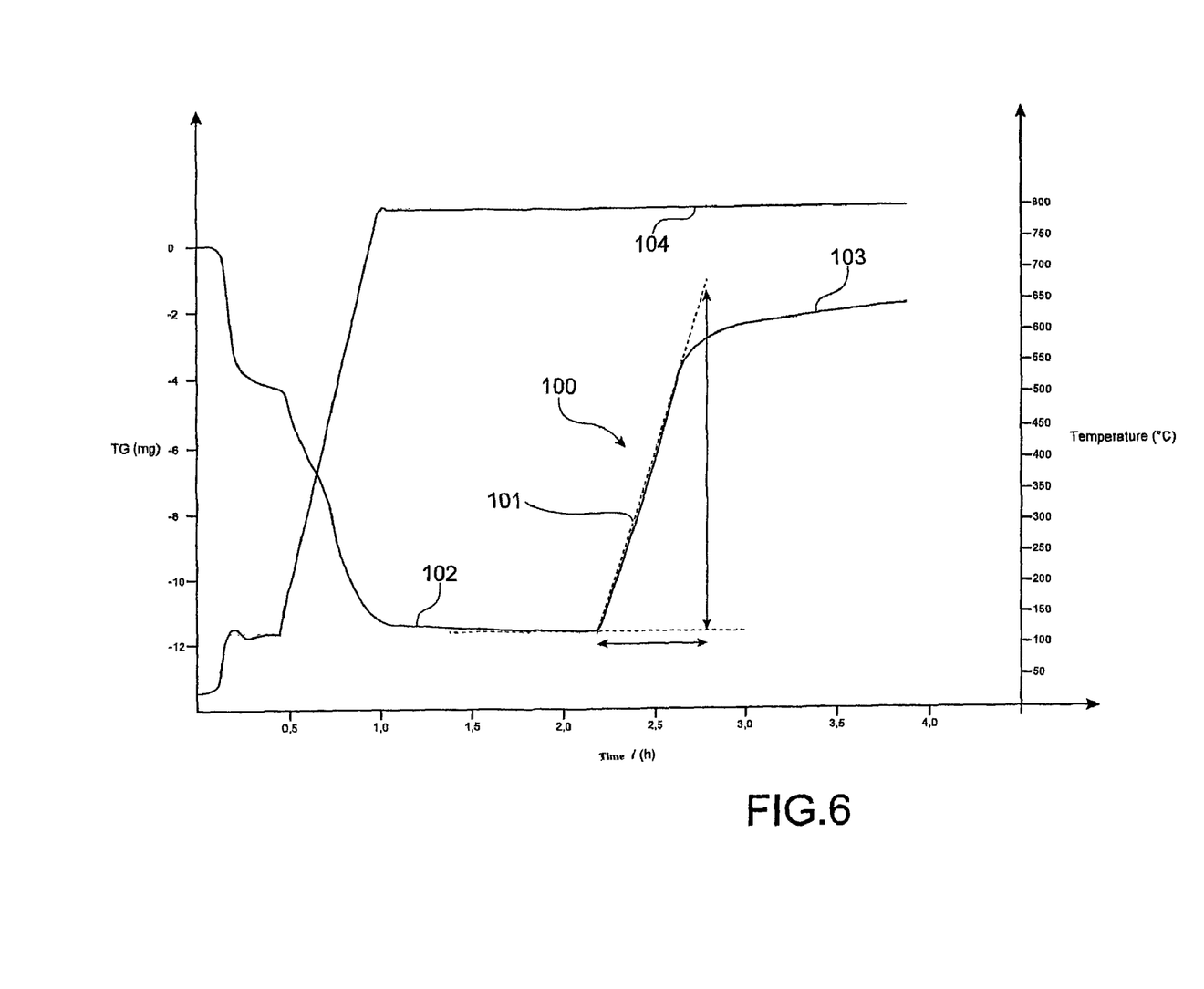
FIG. 6 illustrates a curve of the tracking of coking by micro-weighing for a gas having a constant concentration of tars, toluene having been used as a tracer.

During normal operation, the gas to be analyzed is admitted through the inlet orifice 24 and through the gas homogenization area 25. The gas to be analyzed mixes with the protected gas 26 therein. The device 29 for converging the gas flow to be analyzed directs the flow onto the catalytic body 30 where the catalytic effect of the latter causes coking of the major portion of the gas tars which will be adsorbed at the surface of the latter. As long as the surface of the catalytic body 30 is not entirely covered with a layer of a deposit of hydrocarbon compounds called coke, the contribution of the catalytic effect to the formation of coke is widely above that of the thermal effect. The covering rate may be evaluated by calorimetric measurement or by micro-weighing. In the case when the catalytic body 30 is entirely covered, the thermogravimetric scales 10 are open through its bottom and the assembly 20, 24, 25, 28 and 30 moves down to an automatic sample changer device of the carrousel type which replaces the catalytic body 30 with a new sample. The old sample is then conveyed towards an enclosure in which it will be placed in contact with an oxygen-rich atmosphere in order to carry out combustion of the coke and evaluate the amount of deposited coke via the measurement with a $CO_2$ analyzer. In the case when the catalytic body 30 is not saturated on its first layer (which requires a few hours for tar concentrations of the order of $mg/Nm^3$), the coke deposit causes an increase in the weight which is continuously measured by the thermogravimetric scales 10. The evaluation of the slope of the curve representing the mass increase of the sample versus time (cf. FIG. 6) corresponds to the coking rate measured on the curve 100, more specifically to a strong slope portion 101 between a preliminary inactivity portion 102 and a final portion 103 corresponding to thermal coking. The slope of the portion 101 (here $\Delta m/\Delta t = 0.274$ mg/min) gives the catalytic coking rate. By knowing the coking rate, it is possible after calibration of the thermogravimetric scales 10 to calculate the gas tar concentration in the main flow $\phi_p$. Before carrying out the measurement, the micrometric valves 14 have to be adjusted in order to equalize the gas flows to be analyzed in both thermostatted enclosures of the thermogravimetric scales.

The operation of the coupled analysis system 18 will now be described with reference to FIG. 1.

With an $H_2$ analyzer 18, it is possible to measure the dihydrogen concentration at the exit of the gases from the thermogravimetric scales 10; this measurement combined with the micro-weighing measurement gives elements of response on the composition of the tars. The link between the coking rate and the $H_2$ emission rate may thereby be established, notably resulting from the dehydrogenation of tars which occurs during coking.

Exemplary Embodiment

The different components of the tar measurement device are dimensioned depending on the volume flow rate of gas $\phi_p$ flowing in the main conduit and on the pressure and temperature conditions, respectively $P_p$ and $T_p$ prevailing in the latter.

A dimensioning example is provided below, by considering a volume flow rate of 100 $Nm^3/h$ for a diameter of the main conduit of 1½ inches. The pressure and the temperature prevailing inside the latter are 10 bars and 400° C. respectively.

Outer dimensions of the frit 3: 5 mm×5 mm
Pressure loss of the frit 3 under no load conditions: <0.1 bar
Porosity of the frit 3: 0.1 to 2 μm
Efficiency of the frit 3: 99.9% for a particle diameter above 2 μm.
Maintained temperature of the frit 3: 400° C.
Maintained temperature of the ducts and of the other elements upstream from the thermogravimetric scales: 400° C.
Diameter of the connecting conduits: ⅛ inch or 3 mm;
Sampled gas flow rate $\phi_{d2}$: 0.7 $Nm^3/h$
Volume of the first buffer volume 4: 5 L
Volume of the second buffer volume 6: 10 L
Pressure triggering the safety valves 5 and 7: $P_p+5$ bars
Temperature at the exchanger 8: 20-1000° C.
Size of the diaphragm 9: 1/16 inch or 1.5 mm
Height of the thermogravimetric scales 10: 850 mm
Width of the thermogravimetric scales 10: 500 mm
Length of the thermogravimetric scales 10: 450 mm
Temperature of the liquid coolant: 60° C.
Temperature of the inerting gas: 200-1200° C.
Pressure of the inerting gas: 2.5 bars
Volume flow rate of the inerting gas: 6 $Nm^3/h$
Temperature inside the thermostatted enclosure of the thermogravimetric scales: 200-1200° C.
Pressure inside the thermostatted enclosure of the thermogravimetric scales: 0-4 bars
Diameter of the thermostatted enclosure: 15-20 mm
Coking material: activated alumina
Specific gravity of the activated alumina: 2.8 kg/L
Specific surface area/specific gravity ratio of the catalytic body 30 or 58: 107 $m^5/kg^2$
Temperature at the exchanger 11: 50° C.
Temperature of the condenser 15: −15 to +20° C.
Purge pressure: 4 bars
Sensitivity of the micro-weighing device

The invention claimed is:

1. A device for continuous measurement of the tar concentration in a gas, comprising
a conduit (87) for sampling a partial flow of gas connected to a gas duct enclosure,
and scales (10, 95) to which the conduit leads, and from which is suspended a catalytic body (30, 58) used as a support for coking tars, the catalytic body being enclosed by and being mobile in the gas duct enclosure (91, 97)
wherein said scales comprise a beam having an end and an opposite end, and
wherein the end is weighted down by the catalytic body and the opposite end is weighted down with a non-catalytic body having the same weight as the catalytic body before a measurement is performed.

2. The measurement device according to claim 1, characterized in that it further comprises a thermostatted oven (36, 31) around the catalytic body (30, 58).

3. The measurement device according to claim 1 characterized in that it further comprises a device (8) for adjusting the temperature of the gas in the sampling conduit (87) upstream from the scales.

4. The measurement device according to claim 3, characterized in that the sampling conduit (87) is heat-insulated and maintained at a temperature.

5. The measurement device according to claim 1, characterized in that the body (30, 58) includes a specific surface area/specific gravity ratio above 50 $m^5/kg^2$.

6. The measurement device according to claim 1 characterized in that it further comprises a flow concentrator (29, 53) located around the catalytic body and a flow homogenizer (25) upstream from the flow concentrator.

7. The measurement device according to claim 1 characterized in that it further comprises at least one buffer capacity (4, 6) located on the sampling conduit (87).

8. The measurement device according to claim 1 wherein the beam is an oscillating symmetrical beam and the catalytic body and the non-catalytic body are directly mounted to the beam.

9. The measurement device according to claim 1
wherein the catalytic body and the non-catalytic body are magnetically associated with the beam; and
wherein the measurement device further comprises a thermostatted enclosure under the catalytic body and a recovery aperture, wherein the recovery aperture extends inside the thermostatted enclosure.

10. The measurement device according to claim 9, characterized in that it further comprises a mobile device (59) for changing the catalytic body (58) comprising capacity cells of the catalyst body, mobile between the aperture and a station for changing catalytic bodies.

11. The measurement device according to any of claim 1 characterized in that it further comprises an auxiliary sensor (18) for measuring the concentration of a gas produced during coking downstream from the body and located on a conduit (113) for discharging the partial flow of the gas.

12. The measurement device according to claim 8 characterized in that it further comprises a system for an optical colorimetric measurement (56) of the body.

13. The measurement device according to claim 12, characterized in that the optical colorimetric measurement system (56) is designed for conducting differential measurements on the catalytic body and on the non-catalytic body.

14. The measurement device according to claim 1 characterized in that it further comprises an oven (54) receiving the catalytic body (58) designed for carrying out combustion of the coke and provided with a $CO_2$ sensor (52).

15. The measurement device according to claim 1 characterized in that it further comprises a filter of solid particles (3) at a portion upstream from the sampling conduit (87).

16. The measurement device according to claim 15, characterized in that it further comprises a device assigned to measurement of concentration of tars in the solid phase and located in front of the solid particle filter (3).

17. The measurement device according to claim 16, characterized in that the auxiliary device comprises a trap (2) for solid particles, capable of being weighed.

18. The measurement device according to claim 16, characterized in that the auxiliary device comprises a cyclone (1) for sorting particles.

* * * * *

UNITED STATES PATENT AND TRADEMARK OFFICE
CERTIFICATE OF CORRECTION

PATENT NO. : 7,968,055 B2
APPLICATION NO. : 12/518316
DATED : June 28, 2011
INVENTOR(S) : Meryl Brothier et al.

Page 1 of 1

It is certified that error appears in the above-identified patent and that said Letters Patent is hereby corrected as shown below:

In Column 17, line 34, please delete "calorimetric" and insert therefor --colorimetric--.

In Column 20, line 21, please delete "of" and insert therefor --for--.

In Column 20, line 24, please delete "a" and insert therefor --an auxiliary--.

Signed and Sealed this
Twenty-fourth Day of April, 2012

David J. Kappos
*Director of the United States Patent and Trademark Office*